US00PP30450P3

(12) United States Plant Patent
O'Quinn

(10) Patent No.: US PP30,450 P3
(45) Date of Patent: Apr. 30, 2019

(54) ***TERNSTROEMIA* PLANT NAMED 'BROODY'**

(50) Latin Name: *Ternstroemia gymnanthera*
Varietal Denomination: BROODY

(71) Applicant: Clayton O'Quinn, Fort White, FL (US)

(72) Inventor: Clayton O'Quinn, Fort White, FL (US)

( * ) Notice: Subject to any disclaimer, the term of this patent is extended or adjusted under 35 U.S.C. 154(b) by 0 days.

(21) Appl. No.: 15/732,163

(22) Filed: Sep. 26, 2017

(65) Prior Publication Data

US 2019/0098815 P1 Mar. 28, 2019

(51) Int. Cl.
*A01H 5/00* (2018.01)

(52) U.S. Cl.
USPC ..... Plt./226

(58) Field of Classification Search
USPC ..... Plt./226
See application file for complete search history.

(56) References Cited

PUBLICATIONS

Nursery Magazine—"New Varieties," Feb. 10, 2017 (p. 26) retrieved from the Internet at <https://www.nurserymag.com/article/new-variety/ ).*

* cited by examiner

*Primary Examiner* — Susan McCormick Ewoldt
(74) *Attorney, Agent, or Firm* — Cassandra Bright

(57) ABSTRACT

A new and distinct *Ternstroemia* cultivar named 'BROODY' is disclosed, characterized by distinctive green and cream variegated foliage with a pink flush on new growth. Plants have a compact habit and are not observed to flower. Plants are very well suited for performance in the landscape, including as a specimen plant or a hedge. The new cultivar is a *Ternstroemia*, suitable for ornamental garden purposes.

2 Drawing Sheets

Figure 1:
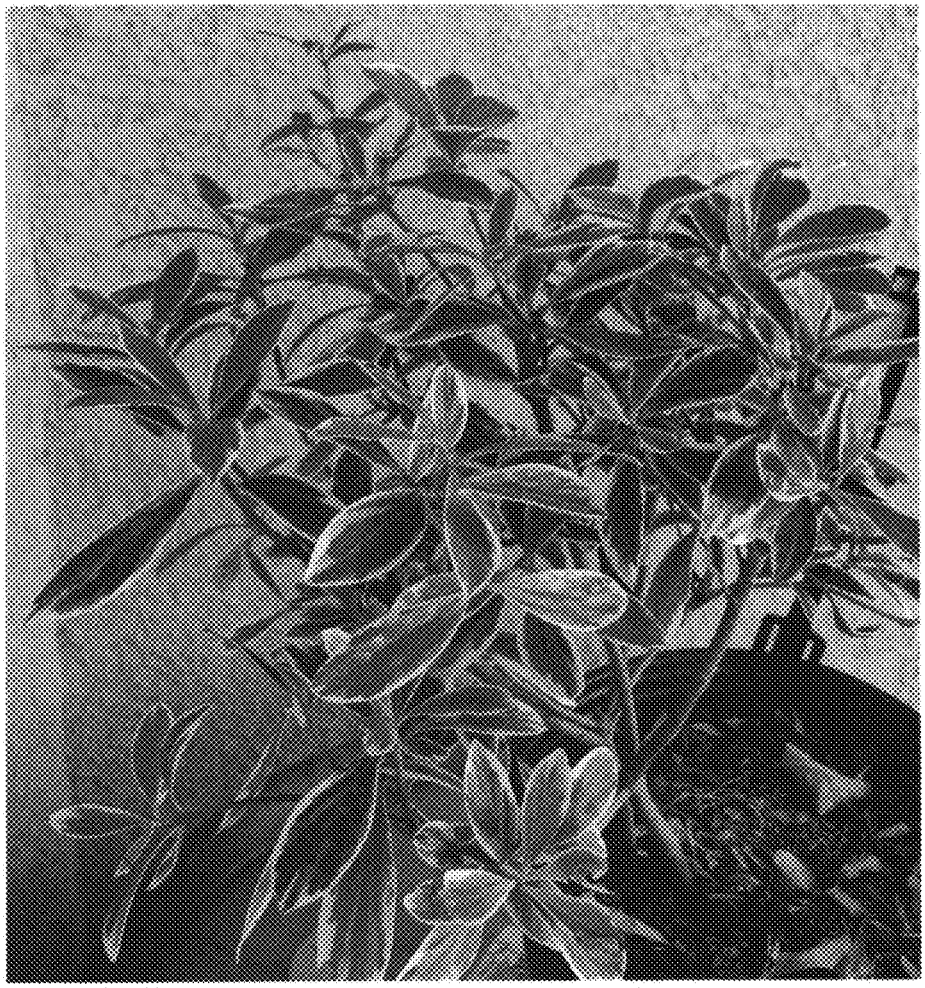

Latin name of the genus and species: *Ternstroemia gymnanthera.*

Variety denomination: 'BROODY'.

BACKGROUND OF THE INVENTION

The new *Ternstroemia* cultivar is a product of chance discovery by the inventor at a commercial nursery in Fort White, Fla. in August of 2006. The inventor discovered the new variety as a single branch, naturally occurring mutation of the parent variety, an unnamed *Ternstroemia gymnanthera.*

After identifying the new variety as a potentially interesting selection, the inventor first organized propagation of 'BROODY' by terminal vegetative cuttings September of 2006 at the same commercial nursery in Fort White, Fla. The inventor continued controlled testing and propagation, assessing stability of the unique characteristics of this variety. At least four generations have been reproduced and have shown that the unique features of this cultivar are stable and reproduced true to type.

SUMMARY OF THE INVENTION

The cultivar 'BROODY' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BROODY' These characteristics in combination distinguish 'BROODY' as a new and distinct *Ternstroemia* cultivar:

1. Unique variegated foliage with yellow margins and pink flushed new foliage.
2. Compact plant.
3. Blooming not observed under normal garden conditions. No fruits of flowers produced regularly.

COMPARISON TO PARENT VARIETY

The new variety is similar to the parent variety in most horticultural characteristics. However, 'Broody' differs from the parent variety in the following:

1. Plants of the new variety are more cold hardy than plants of the parent.
2. Foliage of the new variety is variegated, foliage of the parent is solid.
3. Plants of the new variety are smaller than plants of the parent variety.
4. Foliage of the new variety is less glossy than foliage of the parent.
5. Plants of the new variety rarely bloom, plants of the parent variety bloom regularly.

COMMERCIAL COMPARISON

'BROODY' can be compared to the commercial variety *Ternstroemia gymnanthera* 'Contherann', U.S. Plant Pat. No. 11,737. Plants of the new cultivar 'BROODY' are similar to plants of 'Contherann' in most horticultural characteristics, however, plants of the new cultivar 'BROODY' differ in the following:

1. 'BROODY' has variegated foliage not seen in this comparator.

2. Plants of the new variety rarely bloom and have not been observed to set fruit, plants of this comparator flower and set fruit regularly.
3. Foliage of the new variety produces a pink blush, foliage of this comparator produces a dark bronze blush.
4. Plants of the new variety are smaller than plants of this comparator.

'BROODY' can be compared to the commercial variety *Ternstroemia gymnanthera* 'Sotall', U.S. Plant Pat. No. 13,680. Plants of the new cultivar 'BROODY' are similar to plants of 'Sotall' in most horticultural characteristics, however, plants of the new cultivar 'BROODY' differ in the following;

1. 'BROODY' has variegated foliage, 'Sotall' has dark green solid colored foliage.
2. Foliage of 'BROODY' is smaller than foliage of 'Sotall'.
3. Foliage of 'BROODY' is less glossy than foliage of 'Sotall'.
4. Plant size of 'BROODY' is smaller than plant size of 'Sotall'.

BRIEF DESCRIPTION OF THE PHOTOGRAPHS

The accompanying photograph in FIG. 1 illustrates in full color a 2 year old plant of the new variety in a 3 gallon pot.

Figure 2:
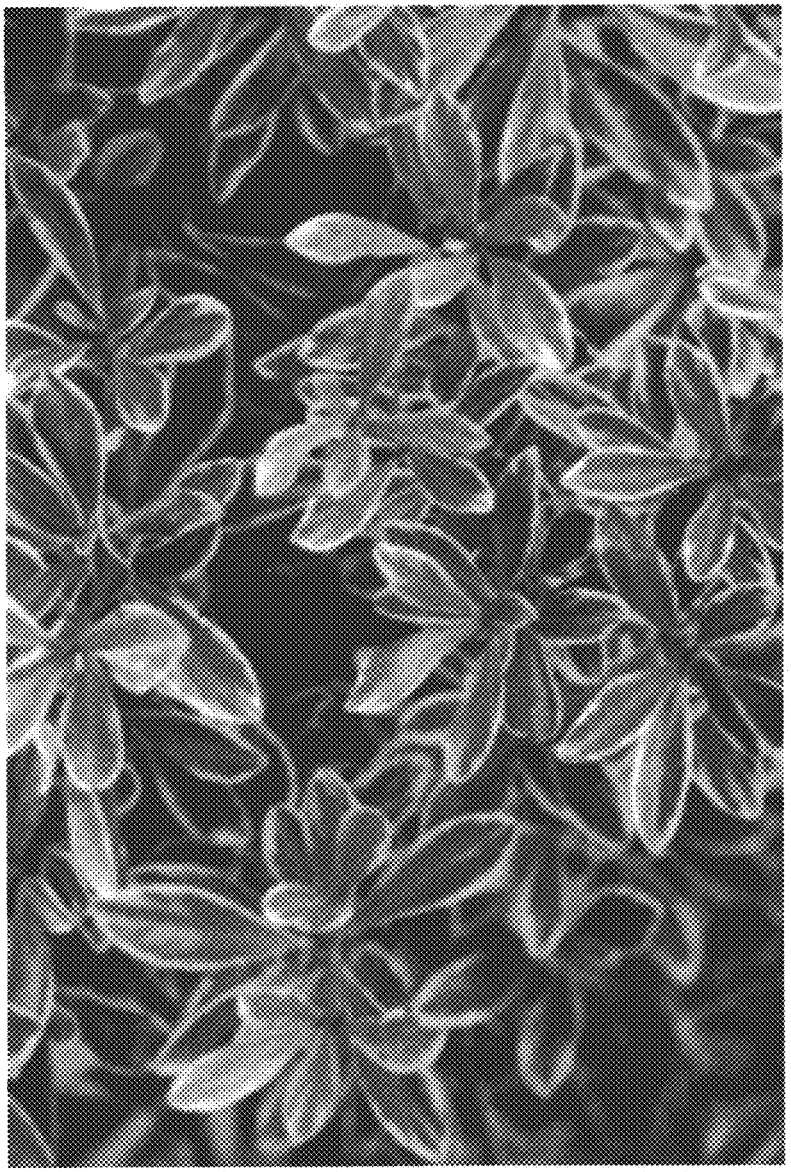

FIG. 2 illustrates new foliage with a pink flush.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BROODY' plants grown outdoors in Loxley, Ala. Plants are approximately 2 years old, in a 3 gallon nursery container. Measurements and numerical values represent averages of typical plant types.

Botanical classification: *Ternstroemia gymnanthera* 'BROODY'.

PROPAGATION

Typically by softwood cuttings in spring and fall.

Root description: Very dense fibrous roots. Colored near RHS Grey-Brown 199C. Somewhat shallow rooted.

PLANT

Growth habit: Globular evergreen shrub.

Height: Approximately 32 cm.

Plant spread: Approximately 36 cm.

Branching characteristics: Moderately well branched, approximately 2 to 4 primary branches from the center of the plant. Branches occur at approximately 45° to 70° angles. Each primary branch has 2 to 4 lateral branches.

Primary branches:

Length of primary branches: Average range 8 to 10 cm, then branching into further laterals.

Diameter of primary branches: Approximately 6 mm.

Primary branch strength: Moderately strong and slightly flexible.

Primary branch color: Oldest wood near RHS Greyed-Purple N187C. Immature branches near Grey-Brown 199A. New Growth near Yellow-Green N144A, flushed Red 45C.

Primary branch texture: Glabrous. Oldest wood somewhat rough, slightly scaly and with lenticels.

*Lenticels*.—Density: Sparse. Shape: Flattened oblong. Size: About 1.5 mm long and 0.8 mm wide.

Lateral branches:

Length of lateral branches: Average range 5 to 10 cm.

Diameter of lateral branches: Average 3 mm.

Lateral branch strength: Moderately strong.

Lateral branch color: Near RHS Grey-Brown 199A.

Lateral branch texture: Slightly rough.

Internode length: Average 1.0 to 2.5 mm.

Age of plant described: Approximately 2 years.

FOLIAGE

Leaf:

*Type*.—Simple.

*Arrangement*.—Alternate or whorl.

*Average length*.—Approximately 4.5 to 5.0 cm.

*Average width*.—Approximately 1.8 to 2.3 cm.

*Shape of blade*.—Spatulate.

*Apex*.—Broad acute.

*Base*.—Attenuate.

*Attachment*.—Sessile.

*Margin*.—Entire.

*Texture of top surface*.—Glabrous.

*Texture of bottom surface*.—Glabrous.

*Appearance of top surface*.—Very glossy.

*Appearance of bottom surface*.—Matte.

*Color*.—Young foliage upper side: Center blotch near Yellow-Green 146A, Margins Yellow 4D. Overall flushed Orange-Red N34C with a slight flush Red 45C near margin. Young foliage under side: Center blotch near Yellow-Green 146A, Margins Yellow 4D. Overall flushed Orange-Red N34C. Mature foliage upper side: Center blotch near Green 143A, Margins Yellow 4C and 4D. Basal dot near Red 45D. Mature foliage under side: Center blotch near Green 137A, Margins Yellow 4D.

Venation:

*Type*.—Pinnate.

*Venation color upper side*.—Same color as leaf blade. Indistinguishable from leaf blade.

*Venation color under side*.—Mid-vein near Green 137B. Lateral veins indistinguishable from leaf blade.

FLOWER

Flowering not observed to date.

OTHER CHARACTERISTICS

Disease and pest resistance: Observed to be more resistant to normal diseases and pests of *Ternstroemia*.

Temperature tolerance: USDA Zone 7 through 10.

Fruit/seed production: Not observed to date.

What is claimed is:

1. A new and distinct cultivar of *Ternstroemia* plant named 'BROODY' as herein illustrated and described.

* * * * *